(12) United States Patent
Ogi (10) Patent No.: US 10,478,046 B2
(45) Date of Patent: Nov. 19, 2019

(54) ENDOSCOPE

(71) Applicant: OLYMPUS CORPORATION, Tokyo (JP)

(72) Inventor: Yoshiyuki Ogi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 308 days.

(21) Appl. No.: 15/475,853

(22) Filed: Mar. 31, 2017

(65) Prior Publication Data

US 2017/0202438 A1 Jul. 20, 2017

Related U.S. Application Data (63) Continuation of application No. PCT/JP2015/074963, filed on Sep. 2, 2015.

(30) Foreign Application Priority Data

Dec. 25, 2014 (JP) .................................. 2014-263189

(51) Int. Cl.

| A61B 1/00 | (2006.01) |
|---|---|
| A61B 1/005 | (2006.01) |
| A61B 1/01 | (2006.01) |
| A61B 1/012 | (2006.01) |
| A61B 1/018 | (2006.01) |

(52) U.S. Cl.
CPC ............ *A61B 1/00137* (2013.01); *A61B 1/00* (2013.01); *A61B 1/0052* (2013.01); *A61B 1/00177* (2013.01); *A61B 1/01* (2013.01); *A61B 1/012* (2013.01); *A61B 1/018* (2013.01)

(58) Field of Classification Search
CPC ..... A61B 1/00137; A61B 1/01; A61B 1/0052; A61B 1/00177; A61B 1/018; A61B 1/012; A61B 1/00121; A61B 1/00128
See application file for complete search history.

(56) References Cited

U.S. PATENT DOCUMENTS

| 4,270,525 A * | 6/1981 | Furihata | ............. A61B 1/00068 600/154 |
|---|---|---|---|
| 5,749,829 A * | 5/1998 | Yokoi | ................ A61B 1/00068 600/153 |

(Continued)

FOREIGN PATENT DOCUMENTS

| CN | 103211565 A | 7/2013 |
|---|---|---|
| JP | S58-054923 A | 4/1983 |
| JP | H10-192229 A | 7/1998 |

OTHER PUBLICATIONS

International Search Report dated Dec. 1, 2015 issued in PCT/JP2015/074963.

*Primary Examiner* — Timothy J Neal (74) *Attorney, Agent, or Firm* — Scully, Scott, Murphy & Presser, P.C.

(57) ABSTRACT

An endoscope includes: a conduit that is provided inside an insertion section and into which a guide wire is inserted in a direction opposite to an insertion direction of the insertion section; a bent conduit that is bent to make the conduit communicate with a pipe sleeve of a treatment instrument insertion port provided in an operation section; and a forceps plug that is detachable from the pipe sleeve. An opening is deviated from a center of the pipe sleeve toward an outer circumferential side of a bending direction of the bent conduit.

10 Claims, 8 Drawing Sheets

(56) References Cited

U.S. PATENT DOCUMENTS

| | | | | |
|---|---|---|---|---|
| 2003/0208104 A1* | 11/2003 | Carrillo, Jr. | A61B 1/00137 | 600/159 |
| 2007/0232859 A1* | 10/2007 | Secrest | A61B 1/00068 | 600/159 |
| 2008/0194913 A1* | 8/2008 | Tinkham | A61B 1/00137 | 600/154 |
| 2010/0087710 A1* | 4/2010 | Weldon | A61B 1/00137 | 600/123 |
| 2010/0280311 A1* | 11/2010 | McGrath | A61B 1/00105 | 600/104 |
| 2013/0253268 A1* | 9/2013 | Okada | G02B 23/2476 | 600/104 |

\* cited by examiner

ENDOSCOPE

CROSS REFERENCE TO RELATED APPLICATION

This application is a continuation application of PCT/JP2015/074963 filed on Sep. 2, 2015 and claims benefit of Japanese Application No. 2014-263189 filed in Japan on Dec. 25, 2014, the entire contents of which are incorporated herein by this reference.

BACKGROUND OF INVENTION

1. Field of the Invention

The present invention relates to an endoscope including a treatment instrument insertion channel into which a treatment instrument is inserted.

2. Description of the Related Art

In recent years, observation and medical treatment have been performed on an affected part in the digestive tract system, the pancreatic and biliary duct system, and the like, with use of an insertion device, for example, a so-called side-view type endoscope (hereinafter simply referred to as an endoscope). The endoscope includes an observation optical system that is provided on a side surface of a distal end portion of an insertion section to be inserted into a subject.

Examples of the treatment for pancreatic and biliary duct system with use of the endoscope may include, in addition to diagnosis treatment in which the biliary ducts or the pancreatic ducts are imaged by an endoscope, examination by an endoscope for the biliary tract that photographs an image inside the biliary ducts (or the pancreatic ducts) and therapeutic treatment in which gallstones in the common bile ducts are removed with use of a balloon, a gripping treatment instrument, and the like.

In such an examination treatment, in some cases, it is necessary to insert, while a distal end of a guide wire is left inside the subject, a proximal end of the guide wire into a treatment instrument insertion channel that is provided in a contrast tube or an insertion section of the endoscope for the biliary tract, and to insert, along the guide wire, the contrast tube or the endoscope for the biliary tract into a papilla.

When the endoscope for the biliary tract is used, the proximal end portion of the guide wire is inserted from the distal end portion of the insertion section of the endoscope for the biliary tract into a treatment instrument insertion channel provided in the endoscope, and is guided out from the treatment instrument insertion port provided in the operation section.

For example, as disclosed in Japanese Patent Application Laid-Open Publication No. 10-192229, an endoscope forceps plug (hereinafter simply referred to as a forceps plug) is attached to the treatment instrument insertion port. The forceps plug prevents sordes and the like inside the body cavity from flowing back through the treatment instrument insertion channel and spouting out when the treatment instrument is not used.

SUMMARY OF THE INVENTION

An endoscope according to an aspect of the present invention includes: a conduit provided inside an insertion section; a pipe sleeve of a treatment instrument insertion port that is provided in an operation section, the operation section being provided on a proximal end side of the insertion section; a bent conduit that is bent to make the conduit communicate with the pipe sleeve; and a forceps plug that is detachable from the pipe sleeve and includes an opening, the opening being deviated from a center of the pipe sleeve toward outer circumferential side of a bending direction inside the bent conduit.

DETAILED DESCRIPTION OF THE PREFERRED EMBODIMENT(S)

The present invention is described below with use of drawings.

Note that, in the following description, the drawings based on an embodiment described below are schematically illustrated. It should be noted that relationship between a thickness and a width of each part, a ratio of thicknesses of each part, and the like are different from actual relationship, an actual ratio, and the like. A part in which the relationship and the ratio of dimensions are mutually different between drawings may be included.

An embodiment of the present invention is described below with reference to the drawings. Note that a side-view type endoscope is described below as an example in the present embodiment.

First Embodiment

Figure 1:
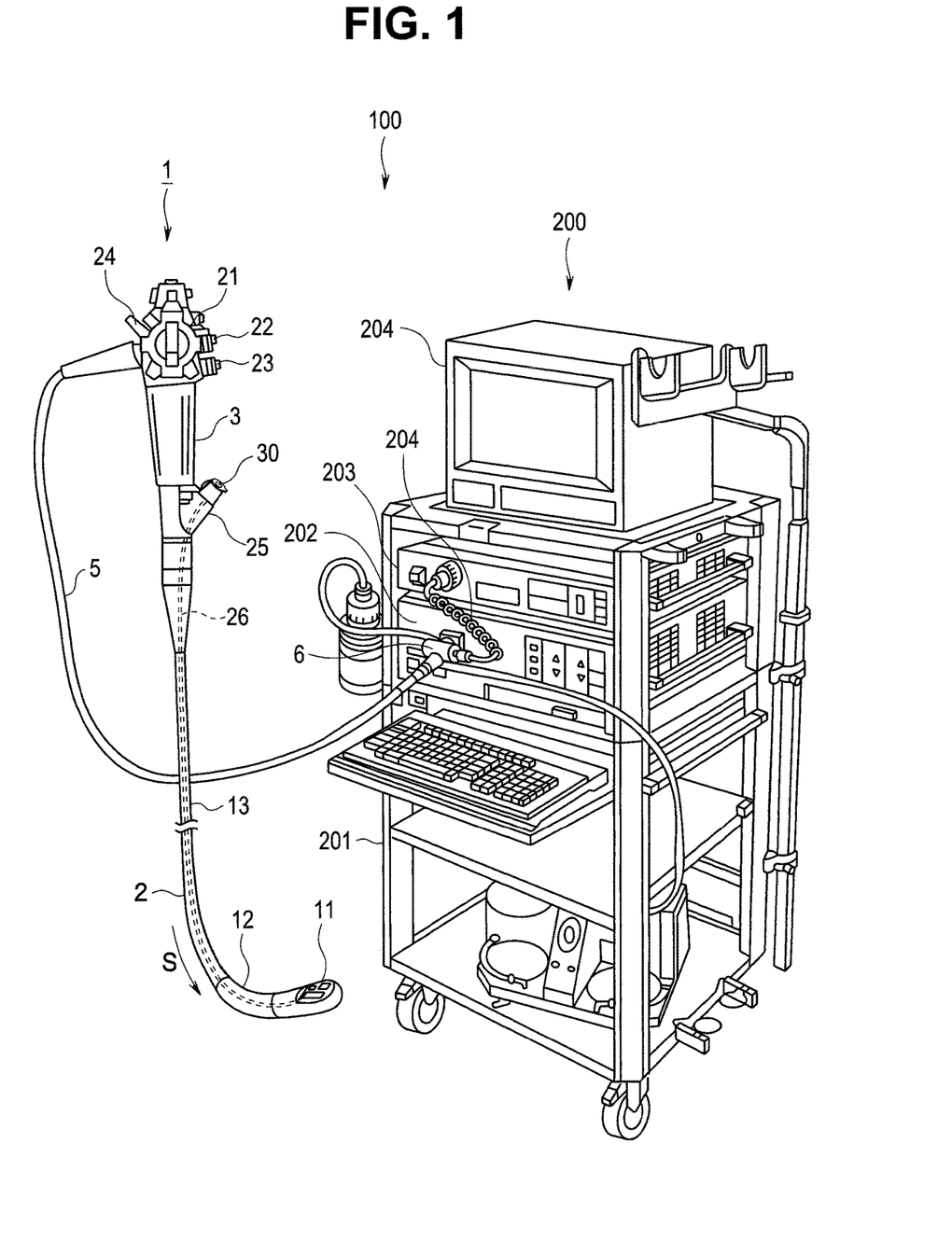
FIG. 1 is a perspective view schematically illustrating an example of an endoscope apparatus that is configured of an endoscope according to an embodiment of an aspect of the present invention and a peripheral apparatus.
Figure 2:
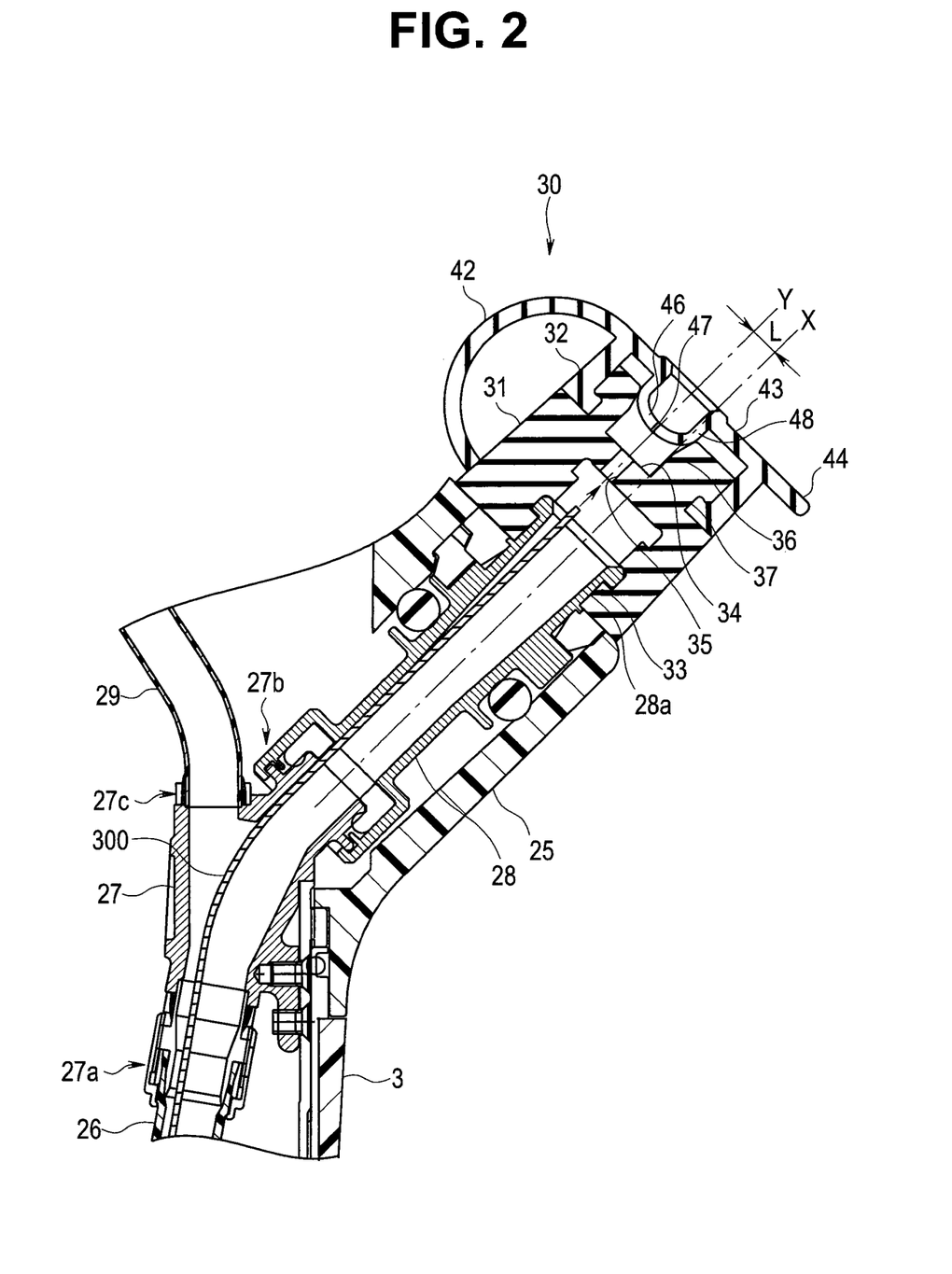
FIG. 2 is a cross-sectional diagram illustrating a configuration of a forceps plug that is attached to a treatment instrument insertion pipe sleeve of a treatment instrument insertion port provided in an operation section according to the embodiment of the aspect of the present invention.
Figure 3:
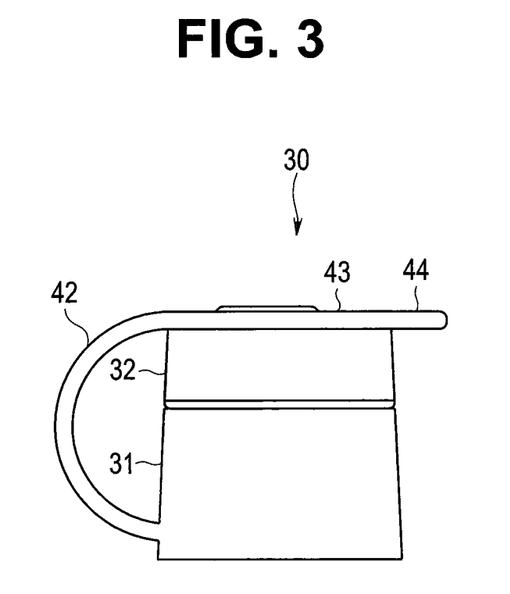
FIG. 3 is a side view illustrating the configuration of a top view of the forceps plug in a state in which a lid-like member engages with a barrel-like member, according to the embodiment of the aspect of the present invention.
Figure 4:
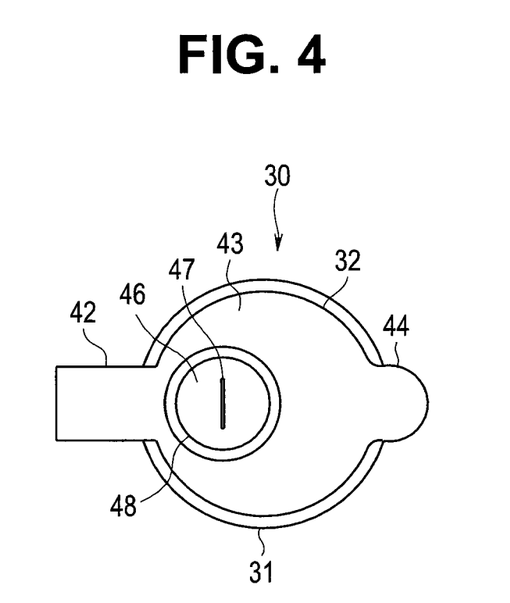
FIG. 4 is a top view illustrating the configuration of the forceps plug in the state in which the lid-like member engages with the barrel-like member, according to the embodiment of the aspect of the present invention.
Figure 5:
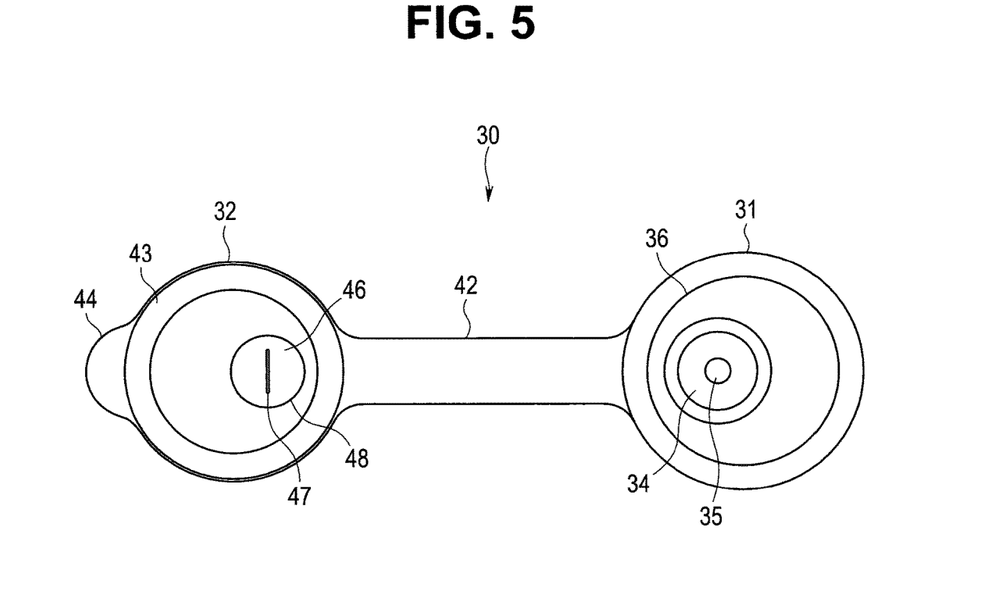
FIG. 5 is a top view illustrating the configuration of the forceps plug in a state in which the lid-like member is released from the barrel-like member, according to the embodiment of the aspect of the present invention.
Figure 6:
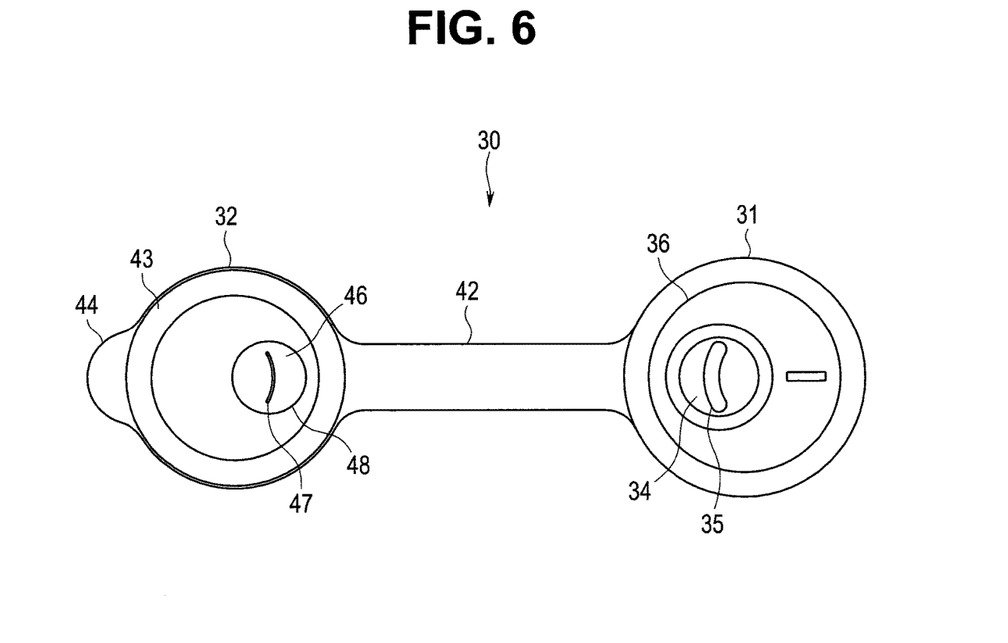
FIG. 6 is a top view illustrating a configuration of a forceps plug in a state in which a lid-like member is released from a barrel-like member, according to a first modification of the embodiment of the aspect of the present invention.
Figure 7:
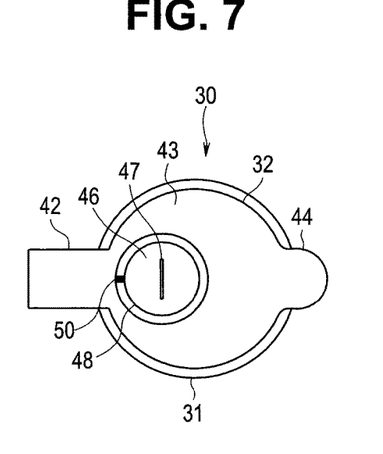
FIG. 7 is a top view illustrating a configuration of a forceps plug in a state in which a lid-like member engages with a barrel-like member, according to a second modification of the embodiment of the aspect of the present invention.
Figure 8:
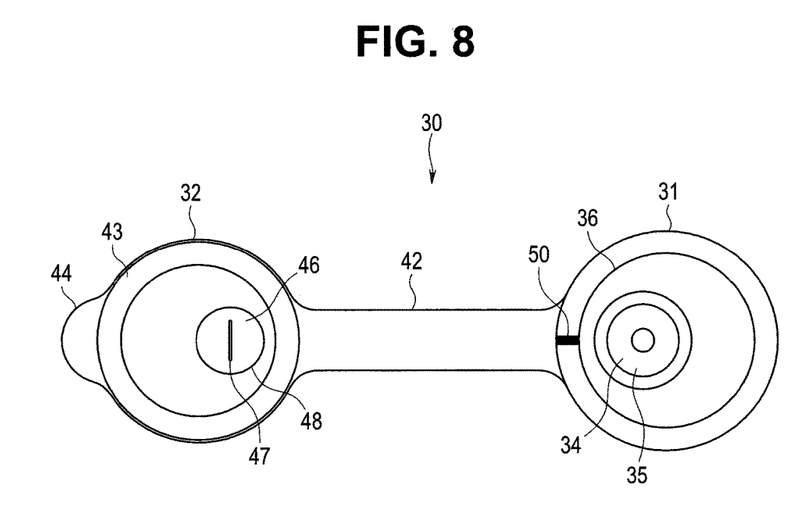
FIG. 8 is a top view illustrating the configuration of the forceps plug in a state in which the lid-like member is released from the barrel-like member, according to the second modification of the embodiment of the aspect of the present invention.
Figure 9:
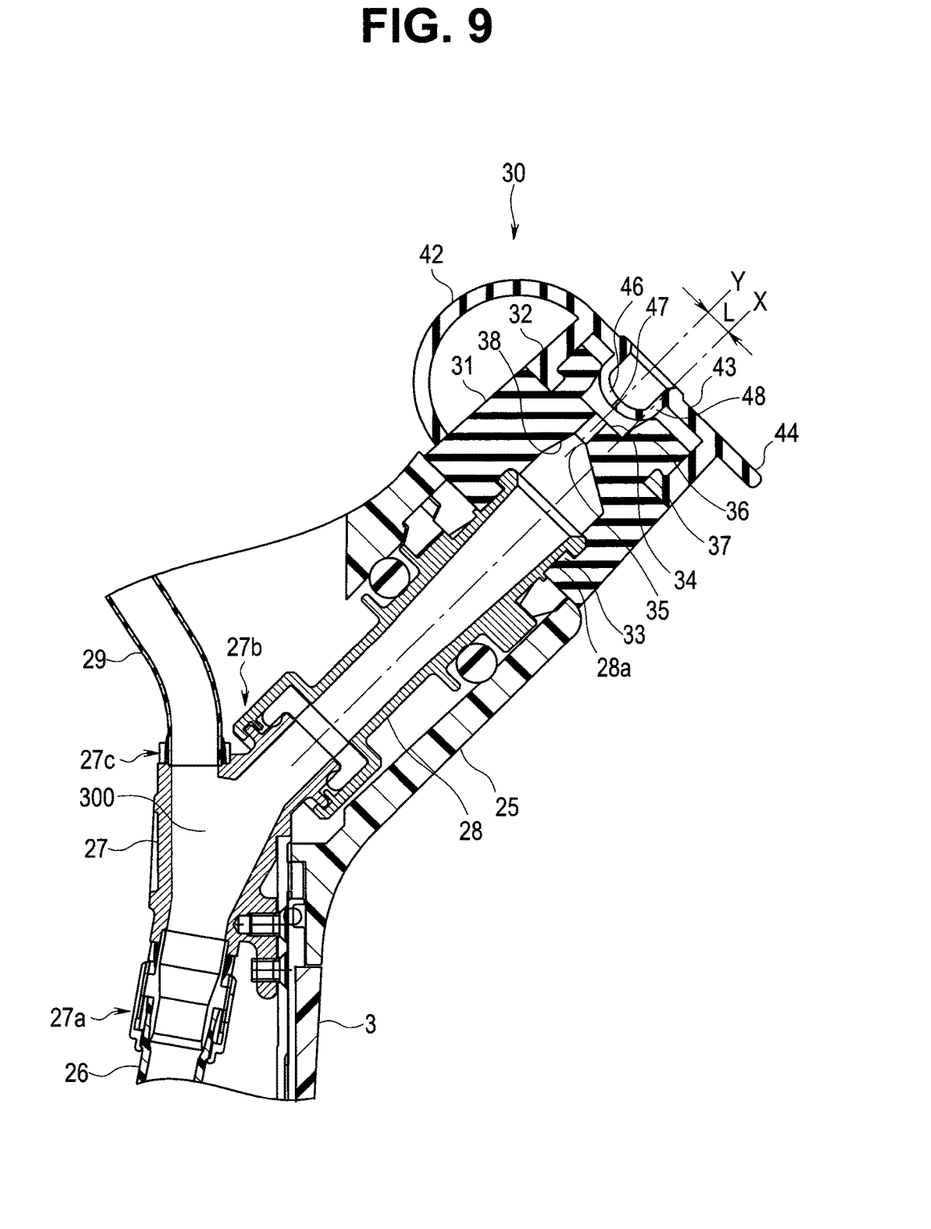
FIG. 9 is a cross-sectional diagram illustrating a configuration of a forceps plug that is attached to a treatment instrument insertion pipe sleeve of a treatment instrument insertion port provided in an operation section, according to a third modification of the embodiment of the aspect of the present invention.
Figure 10:
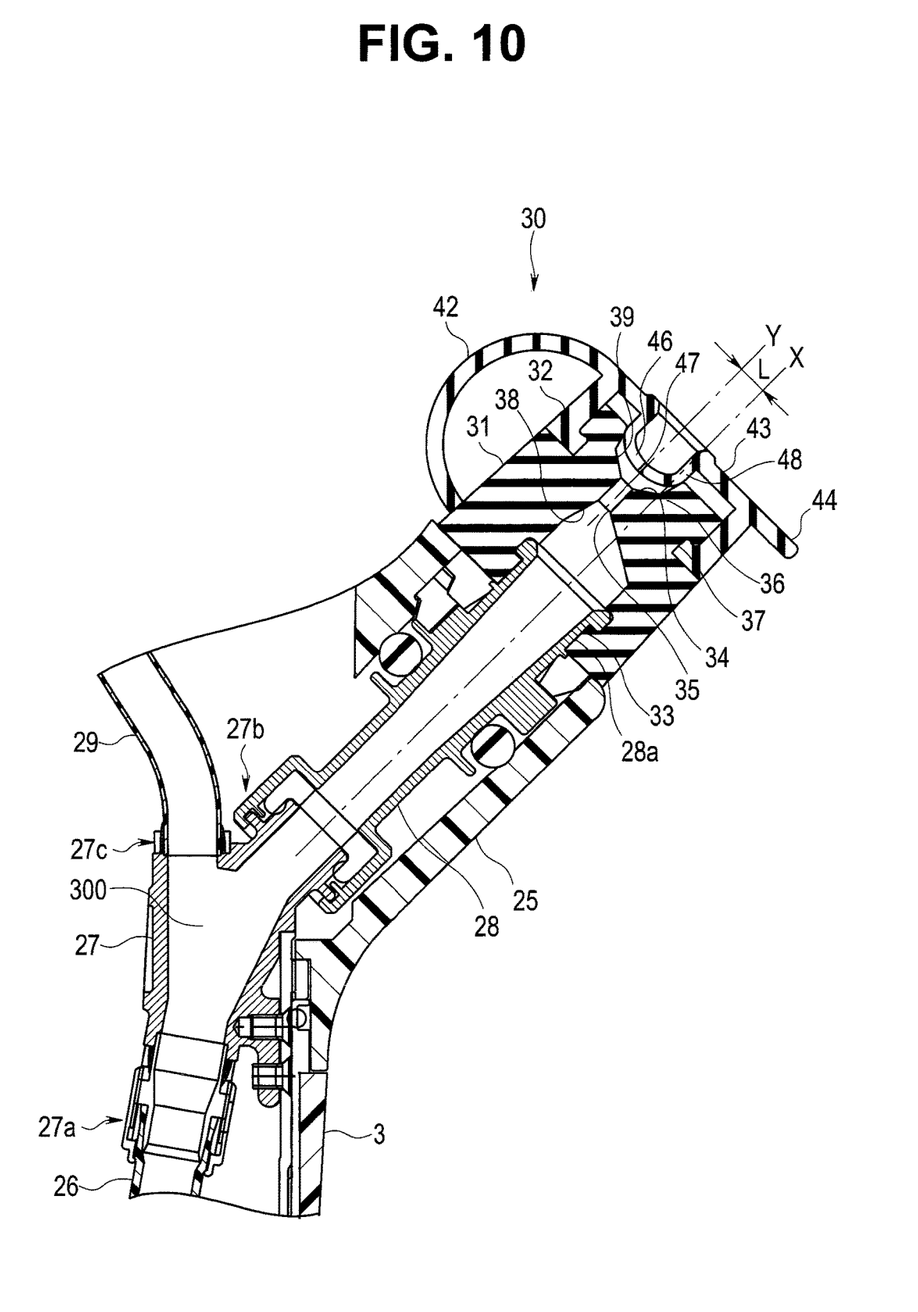
FIG. 10 is a cross-sectional diagram illustrating a configuration of a forceps plug that is attached to a treatment instrument insertion pipe sleeve of a treatment instrument insertion port provided in an operation section, according to a fourth modification of the embodiment of the aspect of the present invention.
Figure 11:
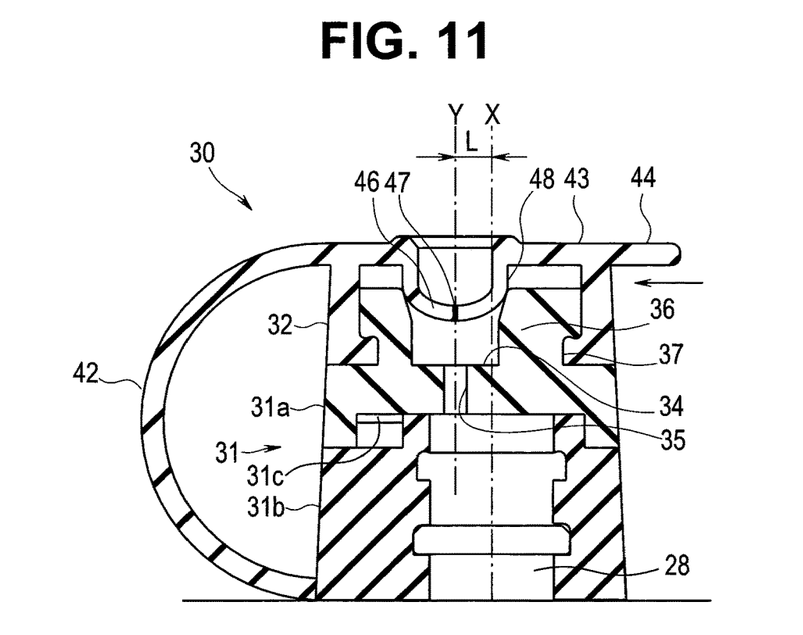
FIG. 11 is a cross-sectional diagram illustrating a configuration of a forceps plug that is attached to a treatment instrument insertion pipe sleeve of a treatment instrument insertion port provided in an operation section, according to a fifth modification of the embodiment of the aspect of the present invention.
Figure 12:
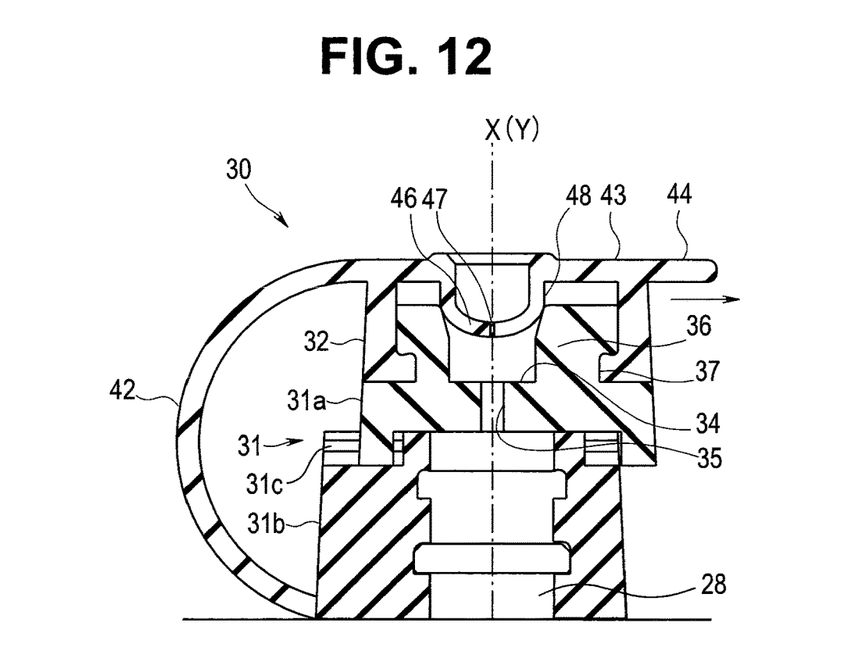
FIG. 12 is a cross-sectional diagram illustrating operation of the forceps plug that is slid from the state of FIG. 11, according to the embodiment of the aspect of the present invention.

FIG. 1 is a perspective view schematically illustrating an example of an endoscope apparatus that is configured of an endoscope according to the present embodiment and a peripheral apparatus. FIG. 2 is a cross-sectional diagram illustrating a configuration of a forceps plug that is attached to a treatment instrument insertion pipe sleeve of a treatment instrument insertion port provided in an operation section. FIG. 3 is a side view illustrating the configuration of a top view of the forceps plug in a state in which a lid-like member engages with a barrel-like member. FIG. 4 is a top view illustrating the configuration of the forceps plug in the state in which the lid-like member engages with the barrel-like member. FIG. 5 is a top view illustrating the configuration of the forceps plug in a state in which the lid-like member is released from the barrel-like member. FIG. 6 is a top view illustrating a configuration of a forceps plug in a state in which a lid-like member is released from a barrel-like member according to a first modification. FIG. 7 is a top view illustrating a configuration of a forceps plug in a state in which a lid-like member engages with a barrel-like member according to a second modification. FIG. 8 is a top view illustrating the configuration of the forceps plug in a state in which the lid-like member is released from the barrel-like member according to the second modification. FIG. 9 is a cross-sectional diagram illustrating a configuration of a forceps plug that is attached to a treatment instrument insertion pipe sleeve of a treatment instrument insertion port provided in an operation section according to a third modification. FIG. 10 is a cross-sectional diagram illustrating a configuration of a forceps plug that is attached to a treatment instrument insertion pipe sleeve of a treatment instrument insertion port provided in an operation section according to a forth modification. FIG. 11 is a cross-sectional diagram illustrating a configuration of a forceps plug that is attached to a treatment instrument insertion pipe sleeve of a treatment instrument insertion port provided in an operation section according to a fifth modification. FIG. 12 is a cross-sectional diagram illustrating operation of the forceps plug that is slid from the state of FIG. 11.

As illustrated in FIG. 1, an endoscope apparatus 100 includes an endoscope 1 and a peripheral apparatus 200. The endoscope 1 includes, as a main part: an insertion section 2 that is inserted into a subject; an operation section 3 that is continuously provided at a proximal end in an insertion direction S of the insertion section 2 (hereinafter simply referred to as a proximal end); a universal cord 5 that is extended from the operation section 3; and a connector 6 that is provided at an extending end of the universal cord 5.

The peripheral apparatus 200 includes a light source device 202, a video processor 203, a connection cable 204, and a monitor 205 that are mounted on a rack 201. The connection cable 204 electrically connects the light source device 202 with the video processor 203.

Further, the endoscope 1 having the above-described configuration and the peripheral apparatus 200 are connected with each other through the connector 6. The connector 6 is connected with, for example, the light source device 202 of the peripheral apparatus 200.

A light guide transmits illumination light from the light source device 202 to an illumination lens of a distal end portion 11 to apply the illumination light into the subject. The illumination lens is described later but is not illustrated in the drawings.

The operation section 3 of the endoscope 1 includes: a bending operation knob 21; an air/water feeding operation button 22; a suction operation button 23; and a raising base operation knob 24 that is pivotally operated to pull or relax a wire that raises or lowers a rising base. The wire is described later. The raising base is provided on the distal end portion 11 but is not illustrated in the drawings.

Furthermore, the operation section 3 includes a treatment instrument insertion port 25 through which a choledochoscope, a treatment instrument, and the like are inserted into a treatment instrument insertion channel 26. The treatment instrument insertion channel 26 is a conduit provided inside the insertion section 2 of the endoscope 1. A forceps plug 30 is attached to the treatment instrument insertion port 25.

The insertion section 2 of the endoscope 1 is configured of, in order from the distal end, the distal end portion 11, a bending portion 12, and a flexible tube portion 13. The bending portion 12 is provided continuously with the proximal end of the distal end portion 11, and the flexible tube portion 13 is provided continuously with the proximal end of the bending portion 12.

The bending portion 12 is so operated to be bent in, for example, four directions of right, left, up, and down by the bending operation knob 21 provided in the operation section 3.

As illustrated in FIG. 2, the forceps plug 30 is detachably attached to a treatment instrument insertion pipe sleeve 28 that is provided at the treatment instrument insertion port 25 of the operation section 3 connected with the treatment instrument insertion channel 26.

Note that the proximal end portion of the treatment instrument insertion channel 26 is coupled with a distal end connection port 27a of a branched tube body 27 through a connection member. The branched tube body 27 serves as a bent member that is a T-shaped tube (also referred to as a K-shaped branched tube) provided and fixed inside the operation section 3.

In addition to the distal end connection port 27a, a treatment instrument pipe sleeve connection port 27b and a suction tube connection port 27c are provided in the branched tube body 27.

The treatment instrument insertion pipe sleeve 28 is connected with the treatment instrument pipe sleeve connection port 27b, and an end portion of a suction tube 29 is connected with the suction tube connection port 27c.

Here, the configuration of the forceps plug 30 according to the present embodiment is described in detail below.

As illustrated in FIG. 2 to FIG. 5, the forceps plug 30 includes a barrel-like member 31 and a lid-like member 32 that are each formed of an elastic rubber material. The lid-like member 32 has a substantially disc-like shape detachable from the barrel-like member 31. Note that the forceps plug 30 is configured such that the barrel-like member 31 and the lid-like member 32 are arranged in series to each other in a state in which the lid-like member 32 is attached to the barrel-like member 31.

As illustrated in FIG. 2, the barrel-like member 31 is attached by being detachably fitted into a circumferential groove 28a that is formed on an outer circumferential surface of the treatment instrument insertion pipe sleeve 28.

In other words, the barrel-like member 31 has an elastic projection 33 projected from an inner circumferential surface of the barrel-like member 31, and the elastic projection 33 is fitted into the circumferential groove 28a that is formed near a port of the treatment instrument insertion pipe sleeve 28.

Further, elastically deforming the vicinity of the elastic projection 33 of the barrel-like member 31 allows the elastic projection 33 to be fitted into or released from the circumferential groove 28a.

The barrel-like member 31 includes a closure film 34 (see FIG. 2 and FIG. 5). The closure film 34 has a small hole 35 serving as an opening, a center of which is formed on an axis (a central axis) Y that is eccentric from a central axis X of the treatment instrument insertion pipe sleeve 28 by a predetermined distance L.

The small hole 35 of the closure film 34 is provided at a position facing an opening end of the treatment instrument insertion pipe sleeve 28 in a state in which the barrel-like member 31 is attached to the treatment instrument insertion pipe sleeve 28.

In other words, the small hole 35 of the closure film 34 is provided at a position that is eccentric from the center of the opening of the treatment instrument insertion pipe sleeve 28 by the predetermined distance L, in the state in which the barrel-like member 31 is attached to the treatment instrument insertion pipe sleeve 28.

Note that the barrel-like member 31 may be preferably provided such that the small hole 35 of the closure film 34 is eccentric at a position along the inner circumferential surface of the treatment instrument insertion pipe sleeve 28.

Further, the choledochoscope, the treatment instrument, and the like, which are not illustrated, are inserted into or removed from the treatment instrument insertion channel 26 through the treatment instrument insertion pipe sleeve 28 and the branched tube body 27 while the choledochoscope, the treatment instrument, and the like push and open the small hole 35 of the closure film 34.

The lid-like member 32 includes a lid portion 43 that is coupled with the barrel-like member 31 through a soft coupling band portion 42. The soft coupling band portion 42 extends from a root part of the barrel-like member 31 (see FIG. 3 to FIG. 5). Further, the lid portion 43 detachably engages with a circumferential groove 37 that is provided on an outer circumferential surface of a neck part of the barrel-like member 31.

A plug body 48 that is provided on and projected from a receiving portion 36 is fitted into the lid portion 43 in a state in which the lid portion 43 engages with the barrel-like member 31. The receiving portion 36 is provided at an inlet of the barrel-like member 31.

The plug body 48 is so provided as to project toward the barrel-like member 31 in the state in which the lid portion 43 engages with the barrel-like member 31.

Note that releasing the lid portion 23 from the circumferential groove 37 makes it possible to draw the plug body 48 from the receiving portion 36. Moreover, a projection 44 that is pinched when the barrel-like member 31 is released is provided on the lid portion 23 (see FIG. 4).

A bottom part of the plug body 48 is configured of a closure film 46, and a slit 47 is provided at a center part of the closure film 46 (see FIG. 4 and FIG. 5). The slit 47 maintains a closed state by elasticity of the slit 47 in a normal state, and is pushed to open, by the choledochoscope, the treatment instrument, and the like that are inserted into or removed from the treatment instrument insertion channel 26.

Note that the slit 47 is provided such that a center part of the slit 47 faces the small hole 35 provided in the closure film 34 of the barrel-like member 31, in the state in which the lid portion 43 engages with the barrel-like member 31.

In other words, as with the small hole 35 of the closure film 34, the slit 47 of the closure film 34 is provided at a position that is eccentric from the center of the opening of the treatment instrument insertion pipe sleeve 28 by the predetermined distance L, in the state in which the barrel-like member 31 is attached to the treatment instrument insertion pipe sleeve 28 and the lid portion 43 engages with the barrel-like member 31.

As mentioned above, the forceps plug 30 having the above-described configuration is attached to-the-treatment instrument insertion pipe sleeve 28 with the predetermined shafting position such that the small hole 35 of the closure film 34 of the barrel-like member 31 and the slit 47 of the closure film 34 of the lid-like member 32 are located on an outer circumferential side in a bending direction of the branched tube body 27 and are eccentric from the center of the treatment instrument insertion pipe sleeve 28 by the predetermined distance L.

Attaching the forceps plug 30 to the treatment instrument insertion pipe sleeve 28 with the predetermined shafting position as mentioned above makes it easy to insert an end part of a guide wire 300 (see FIG. 2) into the small hole 35 of the closure film 34 of the barrel-like member 31 and to easily allow the end part of the guide wire 300 to pass through the forceps plug 30 through the slit 47 of the closure film 34 of the lid-like member 32. The guide wire 300 that has been guided from the distal end portion 11 of the insertion section 2 into the treatment instrument insertion channel 26 in a direction opposite to the insertion direction S (see FIG. 1) passes through the treatment instrument insertion pipe sleeve 28 while being brought close to the outer circumferential side in the bending direction after passing through the branched tube body 27.

As a result, in the endoscope 1 according to the present embodiment, the guide wire 300 that has run back through the treatment instrument insertion channel 26 to reach the treatment instrument insertion pipe sleeve 28 while being brought close to the outer circumferential side in the bending direction by the branched tube body 27, is easily inserted and guided out without being caught by the forceps plug 30.

According to the above description, it is possible for the endoscope 1 according to the present embodiment to allow the guide wire 300 to easily pass through the forceps plug 30 when the guide wire 300 is installed.

Modifications

The forceps plug 30 described above may have any of configurations of various modifications described below. Note that the modifications described below may be combined in configuration.

First Modification

As illustrated in FIG. 6, in the forceps plug 30 according to the present modification, the small hole 35 of the closure film 34 of the barrel-like member 31 is formed in an arc shape. The slit 47 of the closure film 34 of the lid-like member 32 is also formed in an arc shape correspondingly.

Note that the small hole 35 and the slit 47 are provided such that the directions of the respective arc of the small hole 35 and the slit 47 are coincident with the circumferential direction of the treatment instrument insertion pipe sleeve 28 when the forceps plug 30 is attached to the treatment instrument insertion pipe sleeve 28 with the predetermined shafting position.

The above-described configuration makes it possible for the guide wire 300 to easily pass through the forceps plug 30 without being caught by the forceps plug 30.

Second Modification

As illustrated in FIG. 7 and FIG. 8, the forceps plug 30 according to the present modification includes an indicator 50. The indicator 50 is used to determine the predetermined shafting position of the forceps plug 30 when the barrel-like member 31 and the lid-like member 32 are attached to the treatment instrument insertion pipe sleeve 28.

The above-described configuration facilitates determination of the predetermined shafting position of the forceps plug 30 when the forceps plug 30 is attached to the treatment instrument insertion pipe sleeve 28.

Third Modification

The forceps plug 30 according to the present modification has a mortar-shaped tapered surface 38 toward the closure film 34 of the barrel-like member 31.

Such a configuration allows the guide wire 300 to easily pass through the forceps plug 30 without being caught by the forceps plug 30 because the end part of the guide wire 300 is guided to the small hole 35 by the tapered surface 38.

Fourth Modification

The forceps plug 30 according to the present modification has a mortar-shaped tapered surface 39 toward the small hole 35, in addition to the tapered surface 38 according to the third modification. The tapered surface 39 is provided on a surface facing the lid portion 43 of the closure film 34 of the barrel-like member 31, namely, on a surface on side opposite to the tapered surface 38.

Such a configuration allows the choledochoscope, the treatment instrument, and the like to easily pass through the forceps plug 30 because the respective distal ends of the choledochoscope, the treatment instrument, and the like are guided to the small hole 35 by the tapered surface 39 when the choledochoscope, the treatment instrument, and the like are inserted into the endoscope 1.

Fifth Modification

The forceps plug 30 according to the present modification includes a slide mechanism portion that can change the position of the small hole 35 as an opening of the closure film 34, relative to the treatment instrument insertion pipe sleeve 28.

More specifically, as illustrated in FIG. 11 and FIG. 12, in the slide mechanism portion, the barrel-like member 31 includes: a first barrel-like member 31a provided with the small hole 35 of the closure film 34; and a second barrel-like member 31b that is detachably fitted into and attached to the treatment instrument insertion pipe sleeve 28. The first barrel-like member 31a is slidable with respect to the second barrel-like member 31b.

Note that the second barrel-like member 31b has a groove rail 31c that engages with an unillustrated projection of the first barrel-like member 31a and allows the projection to slide while preventing the first barrel-like member from being released from the second barrel-like member 31b.

The first barrel-like member 31a is slidable, with respect to the second barrel-like member 31b, from a position at which the center axis Y of the small hole 35 of the closure film 34 is eccentric from the center axis X of the treatment instrument insertion pipe sleeve 28 by the predetermined distance L illustrated in FIG. 11 to a position at which the center axis Y of the small hole 35 of the closure film 34 is coincident with the center axis X of the treatment instrument insertion pipe sleeve 28 illustrated in FIG. 12.

Such a configuration causes the forceps plug 30 to be switchable between a state in which the forceps plug 30 allows the guide wire 300 to pass through the forceps plug 30 while the small hole 35 of the closure film 34 is brought close to the outer circumferential side of the treatment instrument insertion pipe sleeve 28 and a state in which the forceps plug 30 allows the choledochoscope, the treatment instrument, and the like to be inserted while the position of the small hole 35 of the closure film 34 is returned to the center of the treatment instrument insertion pipe sleeve 28.

Further, returning the position of the small hole 35 of the closure film 34 to the center of the treatment instrument insertion pipe sleeve 28 makes it possible for the forceps plug 30 to have the configuration that does not cause any trouble when the choledochoscope, the treatment instrument, and the like each having a large diameter are inserted.

The invention described in the above-described embodiment is not limited to the embodiment and the modifications, and is variously modified in implementation without departing from the scope of the invention. Further, the above-described embodiment includes inventions in various stages, and various inventions may be extracted from appropriate combination of the plurality of disclosed components.

For example, when the problems to be solved by the invention are solved and the effects described in the advantageous effects of the invention are obtainable even if some components are removed from the all components described in the embodiment, the configuration in which the components are removed may be extracted as the invention.

What is claimed is:

1. An endoscope, comprising:
   an insertion section;
   a conduit provided inside the insertion section;
   a tubular pipe sleeve of a treatment instrument insertion port that is provided in an operation section, the operation section being provided on a proximal end side of the insertion section;
   a bent conduit having a bend with a radius such that the conduit communicates with the pipe sleeve; and
   a forceps plug that is detachable from the pipe sleeve and includes an opening and a lid,
   wherein in a state where the forceps plug is attached to the pipe sleeve, the opening having a center axis offset from a center axis of the pipe sleeve such that the center axis of the opening is eccentric with respect to the center axis of the pipe sleeve in a direction extending outward in a radial direction of the bend in the bent conduit; and
   the lid being detachably disposed over the opening and comprising a slit piercing through the lid.

2. The endoscope according to claim 1, wherein the forceps plug is made of a member having elasticity.

3. The endoscope according to claim 1, wherein the center axis of the opening is provided along an inner circumferential surface of the pipe sleeve.

4. The endoscope according to claim 1, wherein the opening has an arc shape coincident with a portion of a circumference of the conduit.

5. The endoscope according to claim 1, wherein the forceps plug comprises an indicator that is used to determine an attachment position of the forceps plug to the pipe sleeve.

6. The endoscope according to claim 1, wherein the forceps plug includes a first tapered surface provided around a first side of the opening that faces the conduit.

7. The endoscope according to claim 6, wherein the forceps plug includes a second tapered surface provided around the opening on a second side of the opening opposite to the first side.

8. The endoscope according to claim 1, wherein the forceps plug includes a mechanism slidable between a first position and a second position, the first position being at which the center axis of the opening is offset from the center axis of the pipe sleeve, the second position being at which the center axis of the opening is coincident with the center axis of the pipe sleeve.

9. The endoscope according to claim 1, further comprising a guide wire,
wherein the guide wire is inserted into the conduit from a distal end side toward the proximal end side of the insertion section.

10. The endoscope according to claim 9, wherein the guide wire is inserted into the opening.

\* \* \* \* \*